(12) United States Patent
Hudson

(10) Patent No.: US 10,137,311 B2
(45) Date of Patent: Nov. 27, 2018

(54) LIGHT THERAPY GLASSES AND MOBILE APPLICATION

(71) Applicant: Troy Hudson, Runnemede, NJ (US)

(72) Inventor: Troy Hudson, Runnemede, NJ (US)

( * ) Notice: Subject to any disclaimer, the term of this patent is extended or adjusted under 35 U.S.C. 154(b) by 63 days.

(21) Appl. No.: 14/796,363

(22) Filed: Jul. 10, 2015

(65) Prior Publication Data

US 2016/0016004 A1    Jan. 21, 2016

Related U.S. Application Data

(60) Provisional application No. 62/025,572, filed on Jul. 17, 2014.

(51) Int. Cl.
| | |
|---|---|
| *G02C 5/00* | (2006.01) |
| *A61N 5/06* | (2006.01) |
| *G02C 11/04* | (2006.01) |
| *G02C 11/00* | (2006.01) |

(52) U.S. Cl.
CPC .......... *A61N 5/0618* (2013.01); *G02C 5/001* (2013.01); *G02C 11/04* (2013.01); *G02C 11/10* (2013.01); *A61N 2005/0648* (2013.01); *A61N 2005/0652* (2013.01); *A61N 2005/0663* (2013.01); *A61N 2005/0666* (2013.01)

(58) Field of Classification Search
CPC ....... A61N 5/06; A61N 5/0613; A61N 5/0622
USPC .................................. 606/9, 4, 6; 607/88, 91
See application file for complete search history.

(56) References Cited

U.S. PATENT DOCUMENTS

| | | | | |
|---|---|---|---|---|
| 6,319,273 | B1 * | 11/2001 | Chen ...................... | A61N 5/062 128/898 |
| 6,350,275 | B1 * | 2/2002 | Vreman ................ | A61M 21/00 607/88 |
| 7,311,723 | B2 * | 12/2007 | Seibel ...................... | A61F 9/08 128/898 |
| 2012/0203310 | A1 * | 8/2012 | Pugh ..................... | A61M 21/00 607/93 |
| 2016/0158486 | A1 * | 6/2016 | Colbaugh ............ | A61N 5/0618 607/88 |

OTHER PUBLICATIONS

John Brownlee, Google Glass Meets Cyberpunk Light Therapy, May 9, 2014, www.fastcodesign.com/3030381/google-glass-meets-cyberpunk-light-therapy, pp. 1-6.*

* cited by examiner

*Primary Examiner* — Gary Jackson
*Assistant Examiner* — Youwon Kahng
(74) *Attorney, Agent, or Firm* — Panitch Schwarze Belisario & Nadel LLP

(57) ABSTRACT

A portable light therapy device configured to be worn by a patient proximate the eyes includes a front frame including a pair of eye frame sections coupled to each other by a bridge. The bridge is supported on a nose of a patient when worn such that each eye frame section is positioned in front of a respective eye of the patient. A pair of side frames is coupled to opposing ends of the front frame such that, when the device is worn, the side frames extend generally perpendicularly to a plane defined by the front frame. A pair of light modules are each attached to a respective one of the side frames. Each light module includes a light source that emits light and a battery that provides power to the light source, wherein light emitted by each light source is directed into a respective eye of the patient.

9 Claims, 6 Drawing Sheets

LIGHT THERAPY GLASSES AND MOBILE APPLICATION

CROSS-REFERENCE TO RELATED APPLICATIONS

This application claims the benefit of U.S. Provisional Patent Application No. 62/025,572, filed on Jul. 17, 2014, currently pending, entitled "Light Therapy Glasses and Mobile Application," the entire contents of which are incorporated by reference herein.

BACKGROUND OF THE INVENTION

An embodiment of the present invention relates generally to a portable light therapy device, and more particularly, to glasses that enable the user to simulate the effects of sunlight by shining light into the retina.

Light therapy is a very simple process and it involves sitting in front of a light box, such as a flat box with a side of translucent glass or plastic containing an electric light, for a prescribed amount of time each day. The time of use will depend on the patient and intensity of the light source, but the required time is usually from 20-30 minutes each day. Light therapy is most effective in the morning, but can also be used in the afternoon. If used at night, light therapy can cause insomnia.

A patient can read or do other tasks during this time. However, the patient is confined by the seating constraints and the requirement that the artificial light must hit the retina to simulate the effects of sunlight. It is therefore desirable to provide a portable light therapy device that can preferably be worn by the patient to allow for more efficient light direction and adaptation to different lifestyles.

BRIEF SUMMARY OF THE INVENTION

An embodiment of the present invention comprises a portable light therapy device configured to be worn by a patient proximate eyes of the patient. The device includes a front frame including a pair of eye frame sections coupled to each other by a bridge. The bridge is configured to be supported on a nose of a patient when worn such that each of the eye frame sections is positioned in front of a respective eye of the patient. A pair of side frames is coupled to opposing ends of the front frame such that, when the device is worn by the patient, the side frames extend generally perpendicularly to a plane defined by the front frame. A pair of light modules are each attached to a respective one of the side frames. Each light module includes a light source configured to emit light and a battery configured to provide power to the light source, wherein light emitted by each light source is directed into a respective eye of the patient.

Another embodiment of the present invention comprises a portable light therapy device including an eyeglass frame configured to be worn by a patient proximate eyes of the patient, and at least one light source mounted to the frame and configured to emit light that is directed toward retinas in the eyes of the patient.

A further embodiment of the present invention comprises a method of controlling operation of a portable light therapy device worn by a patient proximate eyes of the patient. The method includes providing the portable light therapy device including an eyeglass frame having at least one light source mounted thereto and configured to emit light toward retinas in the eyes of the patient and including a communication module, providing a user interface operated and displayed by a mobile computing device in communication with the communication module of the portable light therapy device, receiving, by the user interface through the mobile computing device, an instruction to turn on the at least one light source, receiving, by the communication module of the portable light therapy device from the mobile computing device, a first command to initiate a supply of power to the at least one light source, and in response to the first command, emitting light from the at least one light source toward retinas in the eyes of the patient.

BRIEF DESCRIPTION OF THE SEVERAL VIEWS OF THE DRAWINGS

The following detailed description of preferred embodiments of the invention will be better understood when read in conjunction with the appended drawings. For the purpose of illustration, there are shown in the drawings embodiments which are presently preferred. It should be understood, however, that the invention is not limited to the precise arrangements and instrumentalities shown.

DETAILED DESCRIPTION OF THE INVENTION

Figure 1:
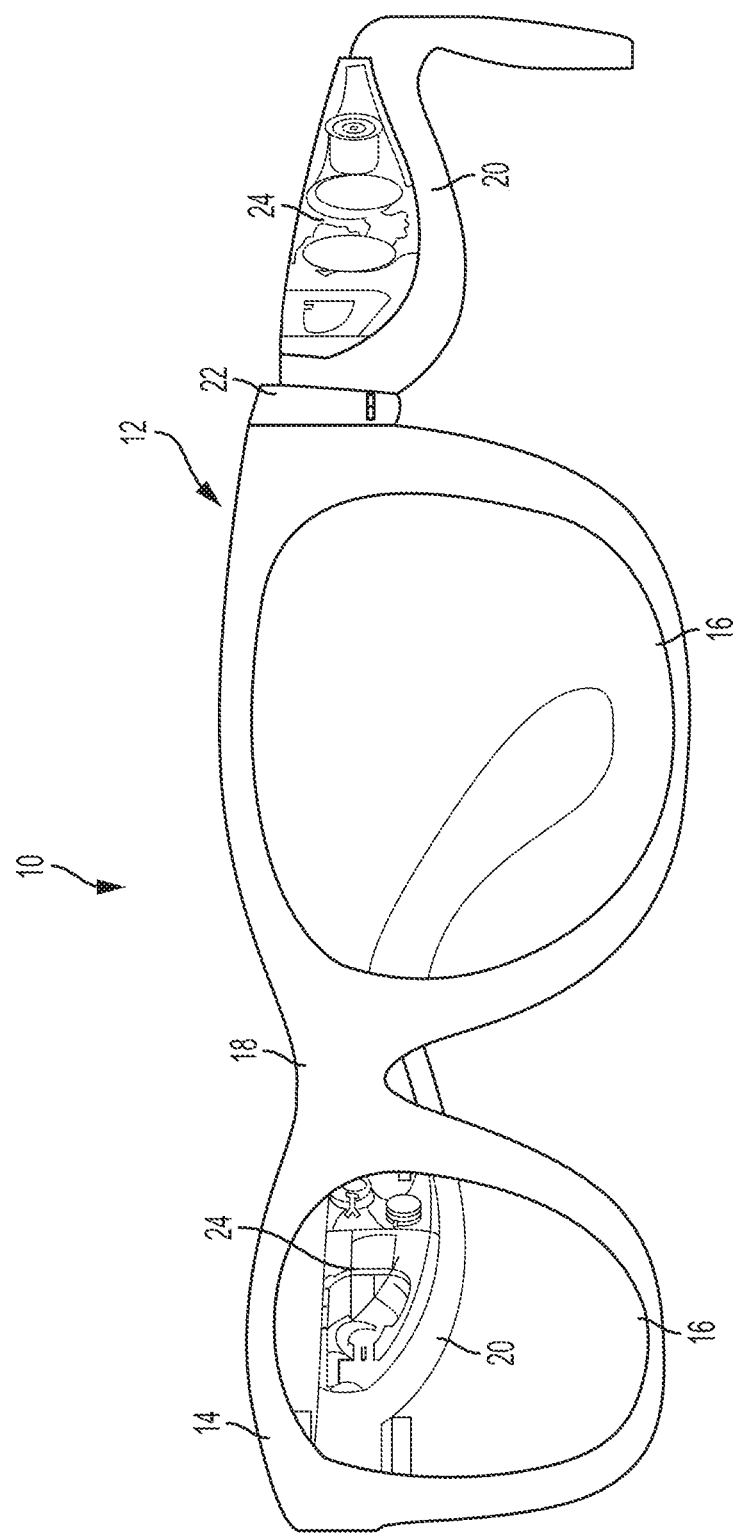
FIG. 1 is a perspective view of light therapy glasses in accordance with a first preferred embodiment of the present invention.

Certain terminology is used in the following description for convenience only and is not limiting. The words "right", "left", "lower", and "upper" designate directions in the drawings to which reference is made. The words "inwardly" and "outwardly" refer to directions toward and away from, respectively, the geometric center of the device and designated parts thereof The terminology includes the above-listed words, derivatives thereof, and words of similar import. Additionally, the words "a" and "an", as used in the claims and in the corresponding portions of the specification, mean "at least one."

Referring to the drawings in detail there is shown in FIG. 1 a first preferred embodiment of light therapy glasses, generally designated 10. The glasses 10 include a frame 12 which may be sized, shaped, and/or configured similar to conventional eyeglass frames. For example, the frame 12 may include a front frame 14 with two spaced apart and generally oval-shaped eye frame sections 16, each of which is configured to rest in front of an eye of the patient.

The eye frame sections 16 may include lenses (not shown) made from glass, plastic, or the like, and/or which are tinted, although the lenses are not necessary, particularly for patients who wear contact lenses or are otherwise not in need of corrective or protective eyewear. The eye frame sections 16 may be connected via a bridge 18 that is configured to be supported on the nose of the patient for proper alignment on the face.

A pair of side frames 20 are preferably attached at opposite sides of the front frame 14 by a hinge 22. The hinge 22 allows the side frames 20 to be moved between a folded configuration, where the side frames 20 extend in a direction generally parallel to a plane defined by the front frame 14, to an open configuration, where the side frames 20 extend in a direction generally perpendicular to the plane defined by the front frame 14, and as shown in FIG. 1. The side frames 20 are generally configured to engage respective ears of the patient for support when the frame 12 is in the open configuration, and may be contoured for comfort. Alternatively, the side frames 20 and front frame 14 can be constructed as one piece of material. The side frames 20 also may be permanently in the open configuration while still in keeping with the inventive concept.

Figure 2A:
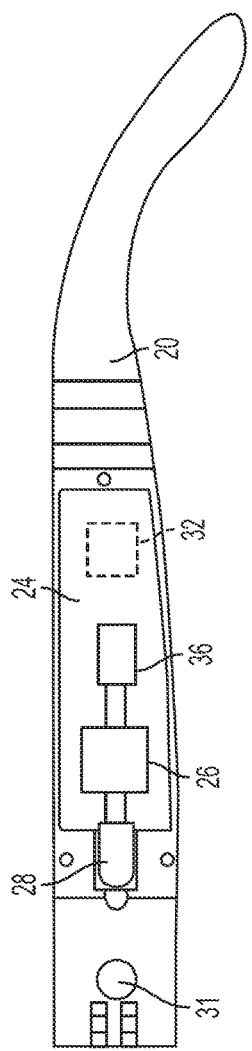
FIG. 2A is a side elevational view of a side frame of the light therapy glasses of FIG. 1.
Figure 2B:
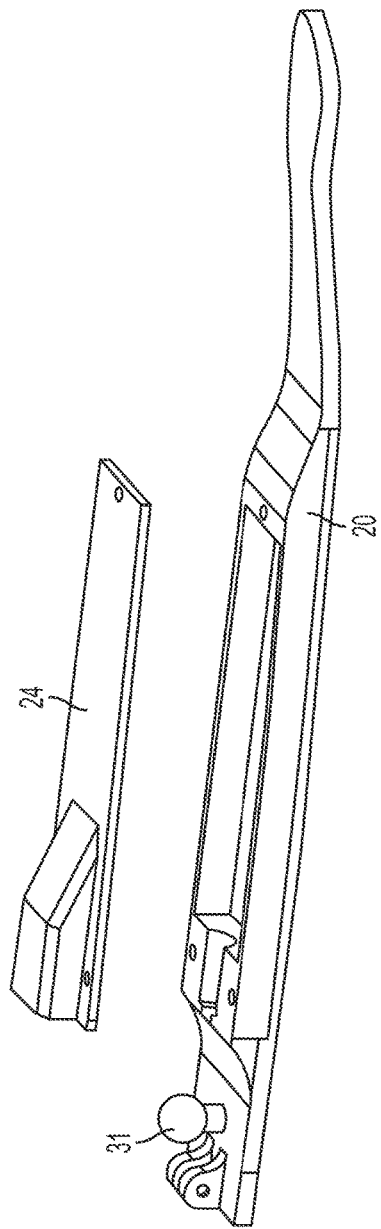
FIG. 2B is an exploded bottom side perspective view of a light module and the side frame of FIG. 2A.

Referring to FIGS. 2A and 2B, a light module 24 is preferably attached to each side frame 20 of the glasses 10. The light module 24 is preferably removably attached to the respective side frame 20 via screws (not shown), clips, friction fit, other mechanical fasteners, or the like. It is preferred that the light modules 24 are detachable for the purpose of charging the batteries 26, as described in further detail below. However, the light modules 24 may instead be, or include portions which are, permanently fixed to the side frames 20. In addition, the light modules 24 or portions thereof may alternatively be mounted to the front frame 14.

The light module 24 is preferably in the form of a case or encapsulant made from clear plastic or the like. One or more light sources 28 are provided in the light module 24, and are preferably light emitting diodes (LEDs). It is preferred that the LEDs 28 emit a blue light, such as having a color temperature of 10,000 Kelvin or above. However, other colors of light, including white light, can be used as well. Where necessary, multiple LEDs 28 can be utilized to create a blended light color. While the embodiment shown in the drawings preferably utilizes LEDs 28, which are preferred for their small size and lower power requirements, other light sources, such as fluorescent, incandescent, or the like may be used as well in keeping with the invention.

The LEDs 28 in each light module 24 are preferably powered by one or more batteries 26 that are also encased within the respective light module 24. The batteries 26 are preferably rechargeable to allow for extended use of the glasses 10, and are preferably of the button-cell type. However, other conventional types of batteries 26 capable of powering the components of the light module 24 without creating undue weight stresses on the glasses 10 or the patient may also be used. A resistor (not shown) or other like component is preferably provided in a circuit between the LEDs 28 and the batteries 26 to limit the power supplied to the LEDs 28. In a preferred embodiment, the power regulating circuit formed by the LEDs 28, the batteries 26, and the resistor or similar component may be housed on a circuit board (not shown) within the light module 24.

In order to recharge the batteries 26, the batteries 26 may be removable, but more preferably a port or other contact is provided so that an external charger (not shown) may be applied. For example, a micro-USB port 32 is shown in FIG. 2A which may be connected to the batteries 26 to allow for recharging. Other types of ports as are conventionally known for charging operations may be used as well.

It should further be noted that while batteries 26 are shown as being located in each side frame 20, it is also contemplated that only one light module 24 on one side frame 20 may house a battery 26, and power could be delivered to the other light module 24 on the opposing side frame by other methods, such as conductive wires contained within the frame 12 or the like.

Figure 3:
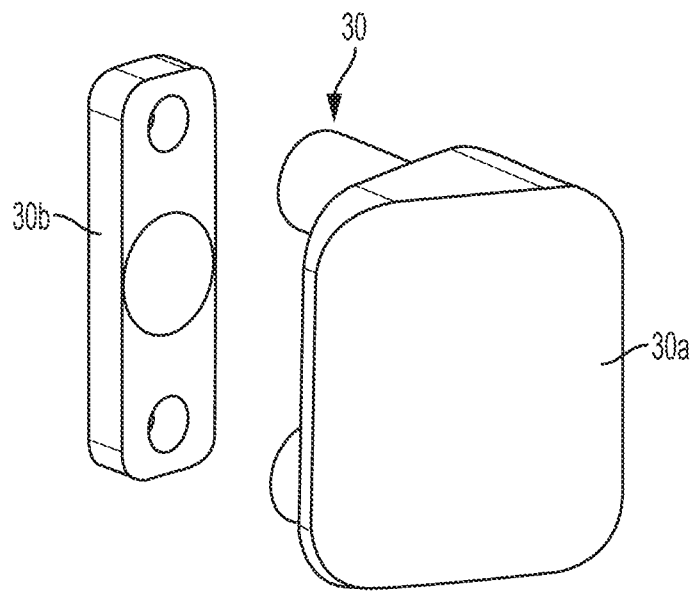
FIG. 3 is an exploded perspective view of a reflector of the light therapy glasses of FIG. 1.
Figure 4:
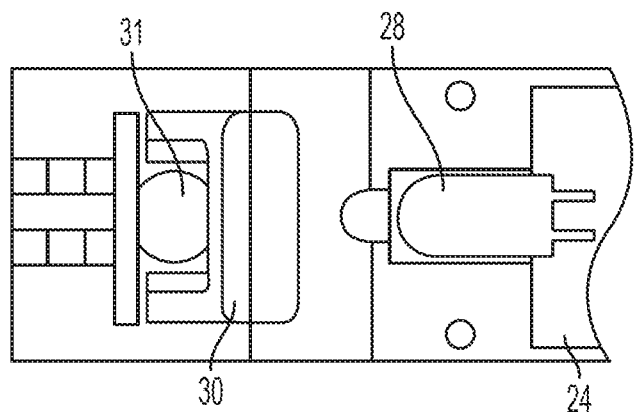
FIG. 4 is a partial side elevational view of the side frame of FIG. 2A with the reflector of FIG. 3 attached thereto.

Referring to FIGS. 3 and 4, it is preferred that a reflector 30 is mounted at an end of each side frame 20 that is proximate to the hinge 22. This arrangement allows for proper directing of the light emitted by the LEDs 28 to the eyes of the patient. The reflector 30 may be a flat, convex, or concave mirror, lens, or like structure. In FIG. 3, the reflector 30 is shown as a flat, angled mirror 30*a* couplable to a base 30*b*. As can be seen in FIG. 4, light from the LEDs 28 is preferably directed forward from the light module 24 and reflected by the reflector 30, which returns a more diffused light into the corners of the retina of the patient. It is preferred that the LEDs 28 provide about 1,000 Lux per side of the frame (a total of 2,000 Lux) to the patient's eyes.

To ensure proper alignment, the reflector 30 may be adjustable within the side frame 20. The reflector 30 preferably rotates 180 degrees to allow customization of the specific angle and direction projecting light into the corner of the patient's retina. In one embodiment, a ball mount 31 may be located near a front of the side frame 20 for mounting the reflector 30. The base 30*b* and the mirror 30*a* of the reflector 30 can be separated and then refastened to one another to surround the ball mount 31. The reflector 30 may be removed to allow movement for positioning of the reflector and can be reattached to the frame 12 to lock in place. Alternatively, the reflector 30 itself may be removable so that adjustments may be made to the ball mount 31 or other receptacle (not shown) on the side frame 20 such that replacement of the reflector 30 results in the proper alignment. In yet another embodiment, the side frames 20 may be manufactured based on prescribed specifications for custom alignment with a particular patient. In keeping with the invention, the reflector 30 may also be mounted in the front frame 14.

In one embodiment of the invention, the reflector 30 may be omitted if the one or more LEDs are mounted to the frame 12 so as to directly emit light toward the retina of the patient.

Referring again to FIG. 2, the light module 24 also preferably includes at least one wireless communication module 36, such as a transceiver configured to communicate according to known wireless transmission schemes, including long range and short range protocols such as BLUETOOTH, BLUETOOTH Low Energy (LE), 802.11 Wi-Fi, infrared, or the like. In the embodiment shown in FIG. 2, the wireless communication module 36 is a BLUETOOTH LE transceiver. The wireless communication module 36 is provided to enable commands, data, or other communications to be exchanged wirelessly between the glasses 10 and an external computing device, such as a mobile phone, tablet computer, laptop computer, desktop computer, server, or the like. In addition, such communications can occur over wired connections, via the micro-USB port 32 or similar conventional ports. In a preferred embodiment, the wireless communication module 36 and/or other communication ports may be commonly housed on the circuit board supporting the power regulating circuit described above.

Figure 5A:
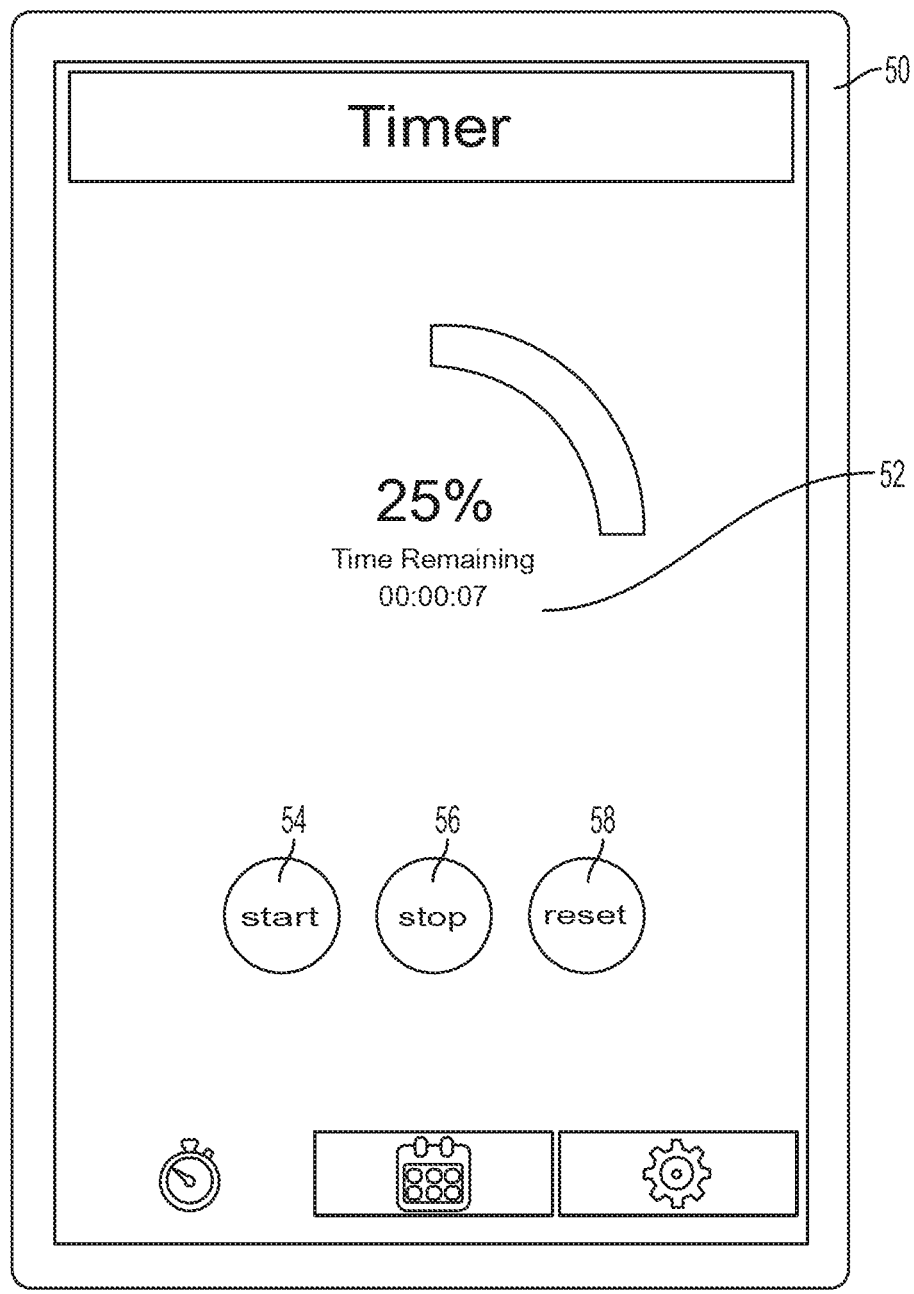
FIG. 5A is a screenshot of a timer page of a mobile application for use with the light therapy glasses of FIG. 1 in accordance with a second preferred embodiment of the present invention.

Referring now to FIG. 5A, a mobile application may be provided that can be used to monitor and/or control usage of the glasses 10 by the patient. The mobile application may be stored and executed on a mobile device 50, such as a mobile phone or the like, although the application may also be configured to run on more traditional type computing devices (e.g., desktop computer or the like). The application may also be stored and executed remotely from the mobile device 50 (e.g., on a remote server or the like) while the mobile device 50 functions as a thin-client display. The mobile device 50 preferably communicates wirelessly with the glasses through the wireless communication module 36 (e.g., via BLUETOOTH).

Figure 5B:
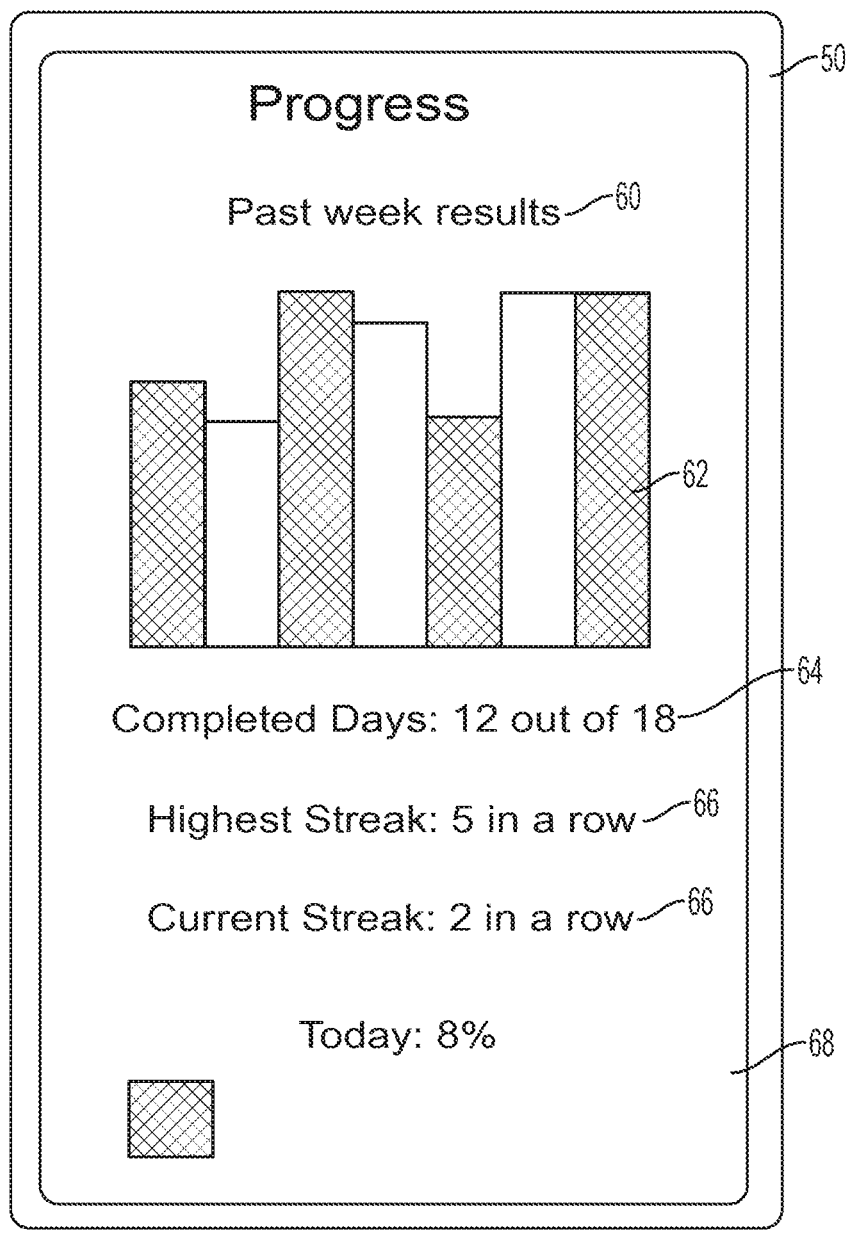
FIG. 5B is a screenshot of a progress page of the mobile application of FIG. 5A.

In FIG. 5A, the mobile application is shown to include a timer 52 that allows the patient to see the time elapsed and also provides the ability to start 54, stop 56, and reset 58 the timer 52. It is preferred that the mobile application, on expiration or pausing of the timer 52, is configured to instruct the glasses 10 to turn off the LEDs 28. This functionality gives the patient the opportunity to remotely control the powering of the glasses 10 to provide the correct amount of light to the patient. The timer 52 also preferably allows the patient to visually monitor the elapsed time or time remaining As shown in FIG. 5B, the mobile application preferably also provides a progress report 60, which is used to keep the patient engaged in the process. For example, the progress report 60 may show the time periods 62 in the previous week during which the glasses 10 were utilized, the number of days 64 the glasses were used, usage milestones 66, active use 68, and the like.

Figure 5C:
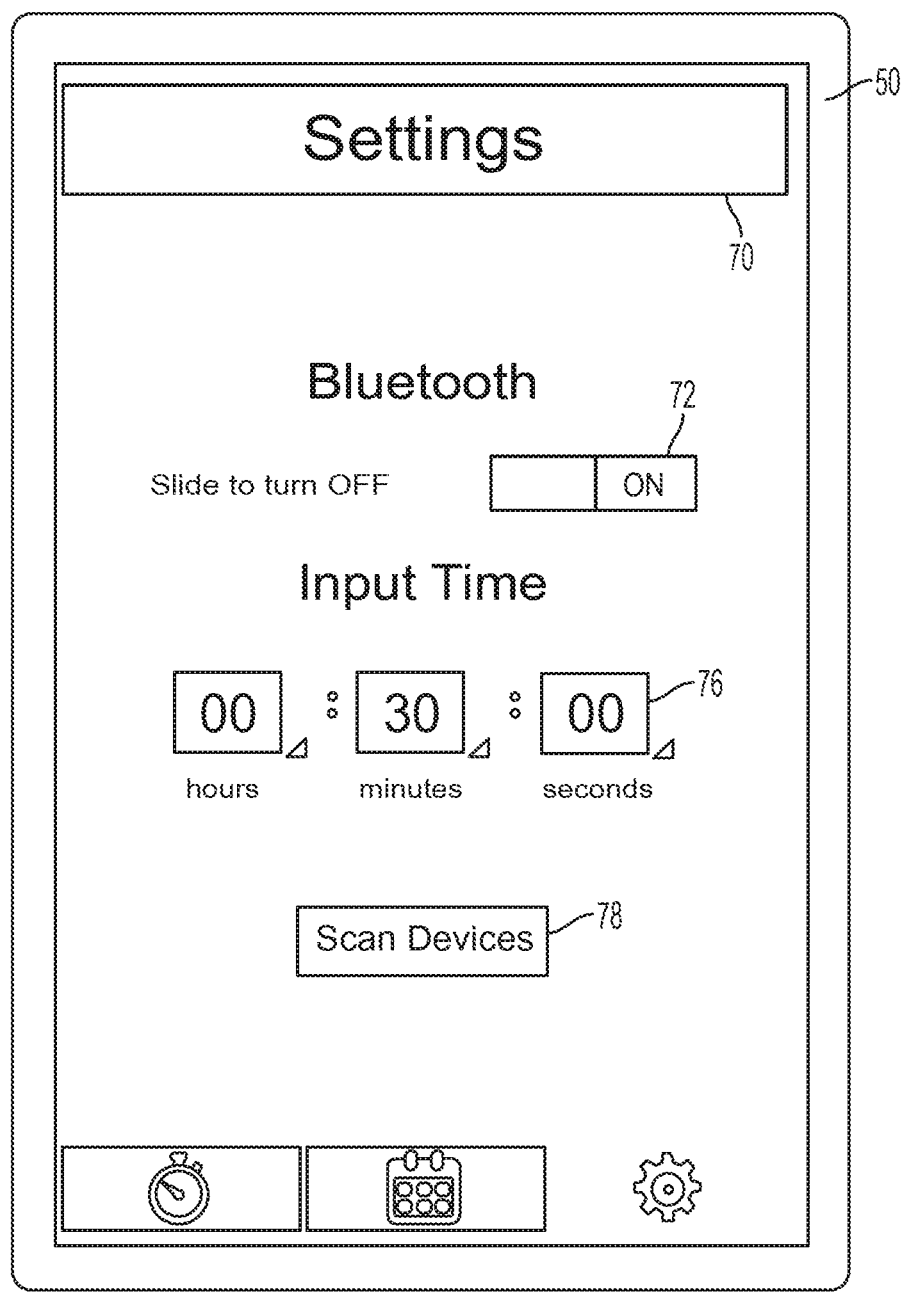
FIG. 5C is a screenshot of a settings page of the mobile application of FIG. 5A.

As shown in FIG. 5C, the mobile application preferably also provides a settings page 70, which can be used to enable wireless communication 72, enable/disable automatic lighting control (not shown), scan for nearby devices 78, and the like. The settings page 70 can also be used to input the prescribed lighting time 76 for the timer 52 in FIG. 5A.

Other pages, controls, and features may also be utilized in the mobile application for controlling and/or monitoring the usage of the glasses 10 in keeping with the invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A portable light therapy device configured to be worn by a patient proximate to the eyes of the patient, the device comprising:
   a front frame including a pair of eye frame sections coupled to each other by a bridge, the bridge being configured to be supported on a nose of a patient when worn such that each of the eye frame sections is positioned in front of a respective eye of the patient;
   a pair of side frames coupled to opposing ends of the front frame such that, when the device is worn by the patient, the side frames extend generally perpendicularly to a plane defined by the front frame;
   a pair of light modules, each of which is attached to a respective one of the side frames, each light module including a light source configured to emit light toward the front frame, and a battery configured to provide power to the light source; and
   a pair of diffuse reflectors, each mounted on a respective one of the side frames proximate the respective light source, wherein the diffuse reflector is configured to direct and diffuse the light emitted by the respective light source into a corner of a retina of a respective eye of the patient.

2. The portable light therapy device of claim 1, wherein a position of each diffuse reflector is adjustable.

3. The portable light therapy device of claim 1, wherein each of the side frames is attached to the front frame via a hinge.

4. The portable light therapy device of claim 1, further comprising a pair of lenses, each of which is disposed within a respective one of the eye frame sections.

5. The portable light therapy device of claim 1, wherein each light source is configured to emit a blue light.

6. The portable light therapy device of claim 1, wherein each light source is at least one light-emitting diode.

7. The portable light therapy device of claim 1, wherein the batteries are rechargeable.

8. The portable light therapy device of claim 1, further comprising at least one wireless communication module attached to one of the front frame or at least one of the side frames.

9. A portable light therapy device comprising an eyeglass frame configured to be worn by a patient proximate to the eyes of the patient, at least one light source mounted to the frame and configured to emit light in a direction away from the eyes of the patient, and at least one diffuse reflector mounted to the frame and configured to direct and diffuse the light from the at least one light source toward corners of retinas in the eyes of the patient.

* * * * *